United States Patent [19]

Hilfenhaus

[11] Patent Number: 4,886,779
[45] Date of Patent: Dec. 12, 1989

[54] INACTIVATION OF HUMAN IMMUNODEFICIENCY VIRUS (HIV) IN PROTEIN-CONTAINING SOLUTIONS BY PHENOLS

[75] Inventor: Joachim Hilfenhaus, Marburg, Fed. Rep. of Germany

[73] Assignee: Behringwerke Aktiengesellschaft, Marburg/Lahn, Fed. Rep. of Germany

[21] Appl. No.: 166,421

[22] Filed: Mar. 10, 1988

[30] Foreign Application Priority Data

Mar. 12, 1987 [DE] Fed. Rep. of Germany ....... 3707987

[51] Int. Cl.$^4$ .............................................. A61K 37/02
[52] U.S. Cl. ...................................... 514/2; 435/236; 435/238; 514/3; 514/6
[58] Field of Search .................... 435/236, 238; 514/2, 514/3, 6

[56] References Cited

U.S. PATENT DOCUMENTS 4,188,375  2/1980  Straub ................................ 435/236
4,711,876 12/1987  Catapano ........................... 514/885
4,713,240 12/1987  Wilkins et al. ........................ 514/2
4,746,508  5/1988  Carey et al. ............................ 514/2

OTHER PUBLICATIONS

Ferrari et al.–Chem. Abst., vol. 105 (1986), p. 57776y.
Eggensperger et al.–Chem. Abst., vol. 98 (1983), p. 59915d.
Avram et al., "Resistance of Bovine Leukosis Virus (BLV) to Various Physical and Chemical Agents," Lucrarile Institutului de Cercetari Veterinare si Biopreparate Pasteur, vol. 16, pp. 69–75 (1982).

Primary Examiner—Sam Rosen
Attorney, Agent, or Firm—Finnegan, Henderson, Farabow, Garrett and Dunner

[57] ABSTRACT

A procedure for the inactivation of human immunodeficiency virus (HIV) in protein solutions as described, which process comprises addition of a phenol to a solution of this type, and allowing it to act. It is possible in this way, for example, to prepare products for human use which are free of any infectious HIV and thus do not transmit AIDS. Phenol is used at a low concentration and can be used at a ph of 3.5 to 4.5.

8 Claims, No Drawings

INACTIVATION OF HUMAN IMMUNODEFICIENCY VIRUS (HIV) IN PROTEIN-CONTAINING SOLUTIONS BY PHENOLS

The invention relates to a process for the inactivation of human immunodeficiency virus (HIV) in protein-containing solutions by the action of a phenol. Preparations treated in this way do not carry the risk of AIDS transmission.

Besides other origins, donated human blood and human plasma proteins given to patients represent a potential source of transmitted in this way of AIDS. The AIDS pathogens which are transmitted in this way are retroviruses the first isolates of which were called LAV, HTLV-III or ARV and are now designated as human immunodeficiency viruses (HIV). There have been described various HIV serotypes. Within the scope of the invention, HIV is to be understood to mean all viruses belonging to this virus group. Whereas the transmission of HIV by human blood as well as by factor VIII concentrates not specially treated for virus inactivation has unequivocally been demonstrated to date HIV transmission by human immunoglobulins has not been found.

However, irrespective of these findings, it is desirable to include process steps leading to inactivation of HIV into the manufacturing procedure of human plasma proteins used for the therapy of human patients. The use of HIV inactivating process steps remains desirable even when there is routine testing of blood donors for antibodies against HIV and the exclusive use of anti-HIV negative donations in order to rule out any potential risk of AIDS transmission due to administration of human plasma protein products. The use of every possible HIV inactivating step when manufacturing human immunoglobulins is desirable in addition to a customary alcohol precipitation.

A HIV inactivating measure of this type must unambiguously inactivate HIV, even where high concentrations are present, and retain the biological activity and specifically of the plasma proteins to be treated. The process should be straightforward and applicable with minimal losses of activity of the plasma proteins. It is disclosed in Lucrarile Institutului de Cercetari Veterinare si Biopreparate "Pasteur" 16, pages 69 to 75 (1982) that bovine leukosis virus, a retrovirus, can be inactivated by incubation in a solution containing 0.5 % phenol for fifteen days.

It has now been found that HIV can be inactivated in aqueous media by phenol and, in particular, by low concentrations which do not adversely affect the activity of, for example, the immunoglobulins.

Thus the invention relates to a process for the inactivation of human immunodeficiency virus (HIV) in protein solutions, which comprises addition of a phenol in a concentration of less than 1 g/100 ml of solution to a solution of this type, and allowing it to act for up to 24 hours.

"Phenol" is to be understood to be an organic chemical compound in which at least one hydroxyl group is directly linked to an aromatic ring system, it being possible for further substituents to be present, such as, for example, in cresols. Phenol itself is preferably used.

It is advantageous to carry out the incubation at room temperature and a pH of 3.5 –4.5 or elevated temperature. Incubation times of 0.5 to 24 hours are appropriate. Incubation is continued until the solution is no longer infectious.

Examples of protein solutions to which the described process can be applied are immunoglobulin solutions or solutions of monoclonal antibodies, "plasma proteins" obtained from natural material or by gene manipulation, such as F VIII, t-PA, urokinase, prourokinase, F XIII and AT III, supernatants from cell cultures or ascites fluid from mice. The process conditions must be such that the properties of the proteins are not changed. Since the stated amount of phenol can be removed without difficulty by standard methods even from preparations of plasma proteins, it is possible to obtain economically by the process according to the invention AIDS safe plasma protein products for human use.

Furthermore, products obtained by the process according to the invention can also be used for diagnostic purposes.

EXAMPLES

HIV inactivation at elevated temperature

Infectious HIV was added to a human immunoglobulin preparation which was free of antibodies against HIV. The virus titer of this mixture was 7.5 $\log_{10}$ ID$_{50}$/ml. The pH was then adjusted to 4, and phenol was added so that the concentration after mixing was 0.3 g/100 ml. After incubation at room temperature for 30 minutes a sample was taken for determination of the virus titer, which had then already decreased to less than 3.5 $\log_{10}$ ID$_{50}$/ml. The phenol-containing virus-/immunoglobulin mixture was further incubated at 40° C. in a water bath for 20 hours and then assayed for infectious HIV. 1 ml samples were free of infectious HIV. This means that HIV inactivation of more than 4 $\log_{10}$ ID$_{50}$ was achieved after incubation for 30 minutes under the stated conditions, and including a further incubation at 40° C. for 20 hours a total inactivation factor of more than 7.5 $\log_{20}$ ID$_{50}$ was obtained.

HIV inactivation at room temperature

A human immunoglobulin preparation free of antibodies against HIV was adjusted to pH 4 and a defined amount of infectious HIV was then added (calculated virus titer of this mixture 5 $\log_{10}$ ID$_{50}$/ml) and, after incubation at room temperature for 15 minsutes, a sample was taken for determination of infectious virus. This titer was 2.8 $\log_{10}$ ID$_{50}$/ml. The resulting inactivation factor was 2,2 $\log_{10}$ ID$_{50}$. Phenol was then added a final to concentration of 0.3 g/100 ml to the virus/immuno-globulin mixture, and the resulting mixture was incubated at room temperature for 30 minutes. Thereafter, infectious HIV was no longer detectable in 1 ml samples of this mixture. Although the low pH partially caused inactivation of HIV, not until phenol was used was complete HIV inactivation (inactivation rate of more than $10^5$) possible.

I claim:

1. A process for the inactivation of human immunodeficiency virus (HIV) in protein solutions with minimal to no adverse effect on the biological activity of the protein solutions, which comprises addition of a phenol to a final concentration of less than about 1 g/100 ml in a protein solution, and allowing the phenol to act for up to 24 hours at a pH of 3.5 -4.5.

2. The process as claimed in claim 1 wherein the phenol is allowed to act at room temperature.

3. The process as claimed in claim 1, wherein the phenol allowed to act at a temprature of 15° to 50° C. until HIV activity is no longer detectable.

4. The process as claimed in claim 1, wherein the phenol allowed to act at a temperature of 35°–45° C. until HIV activity is no longer detectable.

5. A process for the inactivation of human immunodeficiency virus (HIV) in protein solutions with minimal to no adverse effect on the biological activity of the protein solutions, which comprises addition of a phenol to a final concentration of up to about 0.3 g/100 ml in a protein solution, and allowing the phenol to act for up to 24 hours.

6. The process as claimed in claim 5, wherein the phenol is allowed to act at room temperature and at a pH of 3.5 –4.5.

7. The process as claimed in claim 5, wherein the phenol is allowed to act at a temperature of 15°–50° C. until HIV activity is no longer detectable.

8. The process as claimed in claim 5, wherein the phenol is allowed to act at a temperature of 35°–45° C. until HIV activity is not longer detectable.

* * * * *

UNITED STATES PATENT AND TRADEMARK OFFICE
CERTIFICATE OF CORRECTION

PATENT NO. : 4,886,779
DATED : December 12, 1989
INVENTOR(S) : Joachim Hilfenhaus It is certified that error appears in the above-identified patent and that said Letters Patent is hereby corrected as shown below:

Claim 1, col. 2, line 63; "4.5" need not be in boldface;

Claim 4, col. 3, line 2; "phenol" should be followed by --is--.

Abstract, 8th (final) line; "ph" should be --pH--.

Signed and Sealed this

Twenty-first Day of July, 1992

Attest:

DOUGLAS B. COMER

Attesting Officer     Acting Commissioner of Patents and Trademarks